(12) United States Patent
Masuda et al.

(10) Patent No.: US 7,820,037 B2
(45) Date of Patent: Oct. 26, 2010

(54) DESULFURIZING AGENT MANUFACTURING METHOD AND HYDROCARBON DESULFURIZATION METHOD

(75) Inventors: Masataka Masuda, Amagasaki (JP); Shin-ichi Nagase, Sakai (JP); Susumu Takami, Osaka (JP); Osamu Okada, Osakasayama (JP)

(73) Assignee: Osaka Gas Company Limited, Osaka (JP)

( * ) Notice: Subject to any disclaimer, the term of this patent is extended or adjusted under 35 U.S.C. 154(b) by 0 days.

(21) Appl. No.: 12/274,082

(22) Filed: Nov. 19, 2008

(65) Prior Publication Data

US 2009/0071876 A1    Mar. 19, 2009

Related U.S. Application Data

(63) Continuation of application No. 09/913,860, filed as application No. PCT/JP99/00697 on Feb. 18, 1999, now abandoned.

(51) Int. Cl.
*C10G 45/06* (2006.01)
*C07C 5/02* (2006.01)

(52) U.S. Cl. .............. 208/217; 208/208 R; 208/209; 208/211; 208/226; 208/228; 208/230; 208/244; 208/246; 208/247; 208/248; 585/250; 585/257; 585/259; 502/325; 502/326; 502/329; 502/344; 502/345

(58) Field of Classification Search .......... 208/217, 208/244, 246, 247, 208 R, 209, 211, 226, 208/228, 230, 248; 502/325, 326, 329, 344, 502/345; 585/250, 257, 259, 260, 261, 262, 585/266, 267, 269, 270, 275, 160; 505/325, 505/326, 329, 344, 345
See application file for complete search history.

(56) References Cited

U.S. PATENT DOCUMENTS

| | | | | |
|---|---|---|---|---|
| 3,957,962 A * | 5/1976 | Ramsbotham | ............... | 423/655 |
| 4,762,817 A * | 8/1988 | Logsdon et al. | ............. | 502/329 |
| 4,876,402 A * | 10/1989 | Logsdon et al. | ............. | 568/881 |
| 4,891,462 A * | 1/1990 | McMahon | .................. | 585/411 |
| 5,302,470 A * | 4/1994 | Okada et al. | ................... | 429/17 |
| 5,347,021 A * | 9/1994 | Taylor et al. | ................. | 549/325 |
| 5,401,391 A * | 3/1995 | Collins et al. | ........... | 208/208 R |
| 5,482,617 A * | 1/1996 | Collins et al. | ................ | 208/227 |
| 5,626,742 A * | 5/1997 | Brons et al. | .................. | 208/235 |
| 5,635,056 A * | 6/1997 | Brons et al. | .................. | 208/227 |
| 5,637,735 A * | 6/1997 | Tong et al. | ................... | 549/325 |
| 5,685,890 A * | 11/1997 | Okada et al. | .............. | 48/214 A |
| 5,695,632 A * | 12/1997 | Brons et al. | .................. | 208/229 |
| 5,800,798 A * | 9/1998 | Ino et al. | ..................... | 423/654 |
| 5,935,421 A * | 8/1999 | Brons et al. | .................. | 208/226 |
| 6,042,798 A * | 3/2000 | Masuda et al. | ......... | 423/244.01 |

* cited by examiner

*Primary Examiner*—Walter D Griffin
*Assistant Examiner*—Huy-Tram Nguyen
(74) *Attorney, Agent, or Firm*—Stites & Harbison PLLC; Stephen J. Weyer

(57) ABSTRACT

A desulfurizing agent is produced by mixing a copper compound, a zinc compound and an ammonium compound with an aqueous solution of an alkali substance to prepare or precipitate followed by calcitrating the resulting precipitate to form a calcined precipitate into a shape form of a copper oxide-zinc oxide-aluminum oxide mixture. The shaped form is impregnated with iron or nickel and calcined to produce a calcined oxide and reduced with hydrogen to form a sulfur-absorption desulfurizing agent.

17 Claims, No Drawings

DESULFURIZING AGENT MANUFACTURING METHOD AND HYDROCARBON DESULFURIZATION METHOD

CROSS-REFERENCE TO RELATED APPLICATION

The present application is a continuation of U.S. application Ser. No. 09/913,860, filed Sep. 27, 2001, which is a 371 application based on PCT/JP99/00697, filed Feb. 18, 1999, now abandoned, incorporated herein by reference.

TECHNICAL FIELD

The present invention relates to a method for producing a desulfurizing agent for hydrocarbon raw materials in steam reforming processes, or the like, and a method for desulfurizing such hydrocarbon raw materials.

BACKGROUND ART

Various types of hydrocarbons such as natural gas, coal gas (COG), liquefied petroleum gas (LPG) and naphtha, etc., are used as raw materials in steam reforming processes. These hydrocarbons generally contain sulfur. This sulfur poisons catalysts used in the steam reforming process or other processes, and thus lowers the catalytic activity. Accordingly, it is necessary to subject the raw material to a desulfurization treatment in advance.

Conventionally, a typical desulfurization method performed prior to the steam reforming of hydrocarbons is a hydrodesulfurization method comprising the steps of subjecting the organic sulfur contained in the hydrocarbon raw material to hydrogenolysis with using a Co—Mo type or Ni—Mo type catalyst, and removing the hydrogen sulfide thus produced by adsorption on zinc oxide.

However, there are problems in such a conventional method. Specifically, in the hydrodesulfurization process, a certain amount of organic sulfur, especially organic sulfur that is difficult to decompose, such as thiophene, etc., may pass through without being adsorbed on the zinc oxide.

Furthermore, since there are equilibria indicated by (for example)

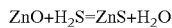

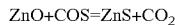

in the adsorption, the amounts of $H_2S$ and COS, etc., likewise do not fall below fixed values. This tendency is especially conspicuous when $H_2O$ and $CO_2$ are present. Furthermore, in cases where the desulfurization system is unstable at the time of start-up or shut-down, etc., of the apparatus, sulfur may also be scattered from the hydrodesulfurization apparatus and adsorption-desulfurizing agent, so that the sulfur concentration in the purified product is increased. Accordingly, the desulfurization process in current steam reforming processes must be controlled at a level which is such that the sulfur concentration in the hydrocarbon after purification is approximately 0.1 ppm.

On the other hand, Ni or Ru catalysts, etc., are used in steam reforming processes. It is known that sulfides are formed on the surfaces of these metals even at low sulfur concentrations of 1 ppm or less. For example, as has been demonstrated by the research of McCarty et al. (McCarty et al.; J. Chem. Phys., Vol. 72, No. 12, 6332, 1980; J. Chem. Phys., Vol. 74, No. 10, 5877, 1981), since the sulfur adsorbing powers of Ni and Ru are extremely strong, even in cases where the sulfur content contained in the raw material is approximately 0.1 ppm, the surfaces of Ni and Ru catalysts are almost completely covered by sulfur in an equilibrium state (sulfur coverage rate of 0.8 or greater). Namely, steam reforming catalysts are extremely sensitive to sulfur, so that such catalysts show a drop in catalytic activity in the presence of even a small amount of sulfur. This means that the sulfur poisoning of steam reforming catalysts cannot be sufficiently prevented at the current level of hydrocarbon desulfurization.

Especially in the case of substitute natural gas manufacturing processes in which methane-rich gases are prepared, since the processes are performed at a low temperature, sulfur is readily adsorbed on the catalyst. Processes are even more sensitive to low concentrations of sulfur. Furthermore, even in steam reforming processes, which are performed at a higher temperature, low concentrations of sulfur have a serious effect in the case where the size of the reaction apparatus must be reduced, as in fuel cell reformers.

Accordingly, in order to prevent sulfur poisoning of the catalyst in subsequent processes and improve the economy of the overall process, it is extremely desirable to minimize the sulfur content in the raw material.

From such a standpoint, Japanese Unexamined Patent Publication No. H1-123627 and Japanese Unexamined Patent Publication No. H1-123628 disclose a method for manufacturing a copper-zinc type desulfurizing agent and a method for manufacturing a copper-zinc-aluminum type desulfurizing agent. When these desulfurizing agents are used, the conspicuous effect of a reduction of the sulfur concentration in the raw material to 1 ppb or less is achieved. However, a large amount of these desulfurizing agents must be used if it is desired to maintain a high level of desulfurization over a long period of time.

On the other hand, it is known that iron and nickel are superior in terms of sulfur adsorption capacity, and that these metals show a superior performance as desulfurizing agents. Accordingly, these metals have been used as desulfurizing agents in several processes.

However, there is a serious impediment to using iron type desulfurizing agents or nickel type desulfurizing agents as is in the desulfurization of steam reforming processes. Specifically, desulfurization in ordinary steam reforming processes is performed in the presence of hydrogen, and this hydrogen is supplied by recycled gas from the outlet port of a reformer. This recycled gas contains CO and/or $CO_2$ as well as hydrogen. Accordingly, in the presence of an iron type or nickel type desulfurizing agent, a reaction of the hydrogen with CO and $CO_2$ (methane forming reaction) occurs, which is accompanied by the problem of a large amount of heat generation.

Japanese Unexamined Patent Publication No. H2-204301 discloses a method in which the abovementioned methane forming reaction is suppressed by causing the raw material to contact a hydrodesulfurization catalyst and a hydrogen sulfide adsorbing agent, and then introducing steam and using a nickel type desulfurizing agent in a steam atmosphere. In this method, however, the following problems arise: specifically, a steam introduction line is required not only for the steam reforming reactor but also for the desulfurization vessel, and as a result of the introduction of steam into the desulfurization vessel, the inherent desulfurization performance of the nickel type desulfurizing agent cannot be fully utilized.

Furthermore, the use of nickel type desulfurizing agents in the absence of hydrogen has also been reported. However, hydrogen is essentially necessary for the decomposition of organic sulfur compounds and the separation of hydrocarbons that contain no sulfur. Supposing that organic sulfur compounds are decomposed in a state in which no hydrogen is present, the deposition of carbon tends to occur on the surface of the nickel desulfurizing agent, leading to a rise in the differential pressure or blocking of the desulfurizing layer, and so forth, over the long term.

DISCLOSURE OF THE INVENTION

Accordingly, a principal object of the present invention is to provide a novel desulfurizing agent which makes it possible to subject hydrocarbon raw materials to a highly effective desulfurization treatment in a stable manner over a long period of time, using a small amount of the agent.

As a result of various studies conducted for the purpose of eliminating or alleviating the abovementioned problems encountered in the background art, the present inventor discovered that, in cases where hydrocarbon raw materials are desulfurized using a copper-zinc-nickel and/or iron type desulfurizing agent and a copper-zinc-aluminum-nickel and/or iron type desulfurizing agent manufactured by a specified method, the concentration of sulfur compounds in various types of gases and oils can be lowered to the ultra-low level of less than 1 ppb (to less than 0.1 ppb under optimal conditions) in a stable manner over a long period of time while suppressing side reactions and the deposition of carbon on the desulfurizing agent.

Specifically, the present invention provides the desulfurizating agent manufacturing method and hydrocarbon desulfurization method described below:

1. A desulfurizing agent manufacturing method which is characterized in that a mixture containing a copper compound and a zinc compound is mixed with an aqueous solution of an alkali substance so that a precipitate is produced, and the precipitate thus obtained is calcined and formed into a shaped form of a copper oxide-zinc oxide mixture, the shaped form is impregnated with iron and/or nickel and further calcined to produce a calcined oxide, and the calcined oxide thus obtained is reduced with hydrogen.

2. The desulfurizing agent manufacturing method according to claim 1, wherein the iron and/or nickel content in the calcined oxide is 1 to 10 wt %.

3. The desulfurizing agent manufacturing method according to claim 1 or claim 2, wherein reduction of the calcined oxide is performed at 150 to 300° C. with using dilute hydrogen gas in which the hydrogen concentration is 6 vol % or less.

4. A desulfurizing agent manufacturing method which is characterized in that a mixture containing a copper compound, a zinc compound and an aluminum compound is mixed with an aqueous solution of an alkali substance so that a precipitate is produced, and the precipitate thus obtained is calcined and formed into a shaped form of a copper oxide-zinc oxide-aluminum oxide mixture, this shaped form is impregnated with iron and/or nickel and further calcined to produce a calcined oxide, and the calcined oxide thus obtained is reduced with hydrogen.

5. The desulfurizing agent manufacturing method according to claim 4, wherein the iron and/or nickel content in the calcined oxide is 1 to 10 wt %.

6. The desulfurizing agent manufacturing method according to claim 4 or claim 5, wherein the reduction of the calcined oxide is performed at 150 to 300° C. using dilute hydrogen gas in which the hydrogen concentration is 6 vol % or less.

7. A hydrocarbon desulfurization method which is characterized in that a hydrocarbon raw material is desulfurized in the presence of hydrogen using the desulfurizing agent described in any of claims 1 through 6.

8. The hydrocarbon desulfurization method according to claim 7, wherein an amount of hydrogen which is such that the hydrogen/hydrocarbon raw material molar ratio is 0.0005 to 0.4 is present.

9. The hydrocarbon desulfurization method according to claim 7 or claim 8, wherein desulfurization is performed at a pressure of 0.05 to 50 atm, a temperature of 100 to 400° C., and a space velocity (GHSV) of 200 to 10,000 $h^{-1}$.

10. The hydrocarbon desulfurization method according to claim 7, wherein the raw material hydrocarbon is town gas, and an amount of hydrogen which is such that the hydrogen/town gas molar ratio is 0.0005 to 0.4 is present.

11. The town gas desulfurization method according to claim 10, wherein desulfurization is performed at a pressure of 0.05 to 50 atm, a temperature of 100 to 400° C., and a space velocity (GHSV) of 200 to 10,000 $h^{-1}$.

12. The town gas desulfurization method according to claim 11, wherein desulfurization is performed so that the sulfur content in the town gas is not more than 5 ppb (vol ppb).

There are no particular restrictions on the manufacture of the copper-zinc-iron and/or nickel type desulfurizing agent (below, "iron and/or nickel" may be abbreviated to X in some cases) and copper-zinc-aluminum-X type desulfurizing agent of the present invention; preferably, however, these desulfurizing agents are manufactured by the processes described below.

The term "mixture of a copper compound and zinc compound" used in the present description includes both a state in which an aqueous solution is formed by mixing a copper compound and zinc compound with water, and a state in which hydroxides are formed by this mixing so that a gel mixture is formed.

(1) Manufacture of Copper-Zinc-X Type Desulfurizing Agent

First, an aqueous solution containing a copper compound (e.g., at least one compound such as copper nitrate or copper acetate, etc.) and a zinc compound (e.g., at least one compound such as zinc nitrate, zinc acetate, etc.) and an aqueous solution containing an alkali substance (e.g., at least one compound such as sodium carbonate, potassium carbonate, etc.) are mixed and agitated, so that a precipitate is produced. The precipitate thus produced is thoroughly washed with water, and is then filtered and dried. Next, the dried precipitate thus obtained is calcined at a temperature of about 270 to 400° C., and water is added to this calcined precipitate to form a slurry, the slurry is filtered, formed and dried to produce a copper oxide-zinc oxide mixed formed body.

The concentration of the copper compound (as copper) in the mixed solution is ordinarily about 0.1 to 1 mol/liter. The zinc concentration (as zinc) in the mixed solution is ordinarily about 0.1 to 1 mol/liter. There are no particular restrictions on the mixture ratio of the copper compound and zinc compound. It is preferable that these compounds be mixed so that the ratio of copper:zinc (atomic ratio) in the mixed solution is about 1:0.3~10; a ratio of about 1:0.5~3 is even more desirable, and a ratio of about 1:1~2.3 is especially desirable.

If necessary, a known binder such as graphite, etc., may be added to the slurry beforehand at the rate of about 1 to 5 wt %.

The forming of the copper oxide-zinc oxide mixture can be performed by an ordinary method such as extrusion forming, tablet forming, granulating, etc., with using the slurry. There are no particular restrictions on the shape or dimensions of the shaped form. Considering the pressure loss, etc., in the process, it is ordinarily desirable to make the shaped form in the form of a spherical shape, a tablet shape, a granular shape, etc., with a size of approximately 2 to 6 mm.

Furthermore, the copper oxide-zinc oxide mixed form may also contain a metal oxide, e.g., chromium oxide, etc., in an amount no greater than about 2 to 3 wt %. In this case, such a metal compound (e.g., chromium oxide, etc.) may be dissolved beforehand in the mixed solution containing the copper compound and zinc compound, or a metal compound that has been separately prepared in advance may be mixed with the mixture containing the copper compound and zinc compound.

The copper oxide-zinc oxide mixed form obtained as described above (in which the atomic ratio of copper:zinc is ordinarily about 1:0.3~10, preferably about 1:0.5~3, and even more preferably about 1:1~2.3) is immersed in an aqueous solution of the X compound (e.g., a nitrate or acetate, etc.), so that the shaped form is impregnated with X atoms. The shaped form is then filtered and dried, the formed body is then calcined at a temperature of about 270 to 400EC in an atmosphere of air. The metal concentration of the X compound in the aqueous solution is ordinarily about 0.01 to 1 mol/liter. It is advisable to adjust the immersion time so that the X oxide content in the copper oxide-zinc oxide mixed sintered body after calcing is about 1 to 10 wt %.

The copper oxide-zinc oxide calcined body obtained as described above is subjected to a reduction treatment at a temperature of approximately 150 to 350° C. in the presence of a mixed gas of hydrogen and an inert gas (e.g., nitrogen gas, etc.) which contains 6 vol % hydrogen or less, preferably approximately 0.5 to 4 vol % hydrogen, thus producing the desired desulfurizing agent.

(2) Manufacture of Copper-Zinc-Aluminum-X Type Desulfurizing Agent

The manufacture of this desulfurizing agent can also be accomplished in the same manner as the manufacture of the above-mentioned copper-zinc-X type desulfurizing agent. First, an aqueous solution containing a copper compound (e.g., at least one compound such as copper nitrate, copper acetate, etc.), a zinc compound (e.g., at least one compound such as zinc nitrate, zinc acetate, etc.) and an aluminum compound (e.g., at least one compound such as aluminum hydroxide, aluminum acetate, sodium aluminate, etc.), and an aqueous solution containing an alkali substance (e.g., at least one compound such as sodium carbonate, potassium carbonate, etc.), are mixed and agitated, so that a precipitate is formed. In this case, it would also be possible to add the aluminum compound to the solution of the alkali substance, and to produce a precipitate by mixing this mixed solution with the mixed solution containing the copper compound and zinc compound. The precipitate thus produced is thoroughly washed with water, and is then filtered and dried. The dried precipitate thus obtained is calcined at a temperature of about 270 to 400° C., and water is added to this calcined precipitate to form a slurry. Next, the slurry is filtered, formed and dried to produce a copper oxide-zinc oxide-aluminum oxide mixed form.

The copper concentration in the mixed solution is ordinarily about 0.1 to 1 mol/liter. The zinc concentration in the mixed solution is ordinarily approximately 0.1 to 1 mol/liter. The aluminum concentration in the mixed solution is ordinarily about 0.03 to 1 mol/liter. There are no particular restrictions on the mixture proportions of the copper compound, zinc compound and aluminum compound; however, the mixture ratio of copper:zinc:aluminum (atomic ratio) in the mixture is preferably about 1:0.3~10:0.05~2, and is even more preferably about 1:0.6~3:0.3~1.

If necessary, a known binder such as graphite, etc., may be added to the slurry beforehand in the range of about 1 to 5 wt %.

The forming of the copper oxide-zinc oxide-aluminum oxide mixed shaped form can be performed by an ordinary method such as extrusion forming, tablet forming, granulating, etc., with using the abovementioned slurry. There are no particular restrictions on the shape or dimensions of the form. Considering the pressure loss, etc., in the process, it is ordinarily desirable to provide the form in the form of a spherical body, a tablet or a granular, etc. having a size of approximately 2 to 6 mm.

Furthermore, the copper oxide-zinc oxide-aluminum oxide mixed formed body may also contain a metal oxide, e.g., chromium oxide, etc., in an amount no greater than approximately 2 to 3 wt %. In this case, such a metal compound (e.g., chromium oxide, etc.) may be dissolved beforehand in the mixture containing the copper compound, zinc compound and aluminum oxide, or an aqueous solution of a metal compound that has been separately prepared in advance may be mixed with this mixture.

The copper oxide-zinc oxide-aluminum oxide mixed formed body obtained as described above (in which the atomic ratio of copper:zinc:aluminum is ordinarily about 1:0.3~10:0.05~2, and is preferably about 1:0.6~3:0.3~1) is immersed in an aqueous solution of the X compound (e.g., a nitrate, an acetate, etc.), so that the formed body is impregnated with X atoms. The formed body is then filtered and dried, after which the formed body is ordinarily calcined at a temperature of about 270 to 400° C. in the atmosphere. The metal concentration of the X compound in the aqueous solution is ordinarily about 0.01 to 1 mol/liter. It is advisable to adjust the immersion time so that the X oxide content in the copper oxide-zinc oxide-aluminum oxide mixed calcined form after calcing is about 1 to 10 wt %, and preferably about 3 to 7 wt %.

The copper oxide-zinc oxide-aluminum oxide B X oxide calcined form obtained as described above is subjected to a reduction treatment at a temperature of about 150 to 350° C. in the presence of a mixed gas of hydrogen and an inert gas (e.g., nitrogen gas, etc.) which contains 6 vol % hydrogen or less, preferably about 0.5 to 4 vol % hydrogen, thus producing the desired desulfurizing agent.

The formed bodies of the copper-zinc-X type desulfurizing agent and copper-zinc-aluminum-X type desulfurizing agent obtained as described above have dense structures consisting of aggregates of fine particles, with extremely small copper particles dispersed on the surfaces of zinc oxide particles. Furthermore, since the copper-zinc and copper-zinc-aluminum formed bodies are impregnated with iron and/or nickel in the range of 1 to 10 wt %, an appropriate amount of iron and/or nickel adheres to and is present on the surfaces of the formed bodies. As a result of iron and/or nickel thus being present on the surfaces of the formed bodies, the amount of iron and/or nickel present inside the formed bodies, which does not contribute to desulfurization, is decreased, so that efficient desulfurization can be accomplished.

Since the amount of iron and/or nickel present on the surfaces of the formed bodies is set at an appropriate amount, copper and iron or copper and nickel are mixed and dispersed very uniformly as fine particles on the surfaces of zinc oxide particles. Accordingly, the formed bodies are in a highly active state as a result of chemical interaction with the zinc oxide. Consequently, side reactions such as methane forming reaction and carbon deposition, etc., which have tended to occur in the case of iron or nickel alone, are suppressed, and a highly active desulfurization performance can be maintained over a long period of time.

On the other hand, in the formed body containing aluminum oxide, the aluminum oxide is uniformly dispersed throughout the formed body as a whole, so that sintering of the fine copper-nickel particles and/or zinc oxide particles by heat is prevented, thus allowing a highly active state to be maintained.

Accordingly, in cases where these desulfurizing agents of the present invention are used, the sulfur content in various types of gases and oils can be reliably lowered to 50 ppb or less; under more desirable conditions, this content can be lowered to 5 ppb or less, and under most desirable conditions, the sulfur content can be lowered to 0.5 ppb or less.

Especially in the case of the copper-zinc-aluminum-X type desulfurizing agent of the present invention, the heat resistance is markedly improved by the action of the aluminum oxide. This leads to the major advantage of a conspicuous alleviation of the drop in strength and the drop in sulfur adsorbing power that occur at high temperatures; accordingly, it is possible for the temperature range in which the agent can be used to be increased.

The desulfurizing agents of the present invention can be used in the same manner as universally known adsorption type desulfurizing agents by (for example) packing an adsorption type desulfurization apparatus of a specified shape with the desulfurizing agent, and passing the gas or oil to be purified through this apparatus.

Specifically, the desulfurization method of the present invention is performed by causing a hydrocarbon raw material to contact the copper-zinc-X type desulfurizing agent (obtained as described above) in a temperature range of approximately 100 to 400° C., or causing such a hydrocarbon raw material to contact the copper-zinc-aluminum-X type desulfurizing agent (obtained as described above) in a temperature range of approximately 100 to 400° C. Preferably, the hydrocarbon raw material is preheated to a predetermined temperature by using a heater or by a method such as heat exchange with the desulfurized gas, etc., prior to desulfurization.

The desulfurization method of the present invention is ordinarily performed by passing a hydrocarbon raw material through a desulfurization tube filled with the copper-zinc-X type desulfurizing agent (or copper-zinc-aluminum-X type desulfurizing agent).

The amount of hydrogen that is added may be determined in accordance with the types and amounts of sulfur compounds that are contained in the raw material. Since the sulfur content is of the order of a few ppm, it is desirable that the amount of hydrogen added be 0.0005 or greater, and preferably 0.001 or greater, in terms of the molar ratio of this hydrogen to the raw-material hydrocarbon. In cases where desulfurization is performed as a pre-treatment for a steam reforming process, a portion of the hydrogen produced by the steam reforming reaction may also be recycled.

The amount of desulfurizing agent that is filled into the desulfurization tube may be appropriately set in accordance with the sulfur content of the hydrocarbon and the conditions of use, etc.; ordinarily, however, this amount may be set so that the GHSV is approximately 200 to 5000 $h^{-1}$ in the case of a gaseous hydrocarbon, and so that the LHSV is approximately 1 to 10 $h^{-1}$ in the case of a liquid hydrocarbon.

In order to suppress the drop in activity of the copper-zinc-X type desulfurizing agent (or copper-zinc-aluminum-X type desulfurizing agent) and thus extend the useful life of the agent, it is desirable to pack the area on the upstream side of the copper-zinc-X type desulfurizing agent packed layer (or copper-zinc-aluminum-X type desulfurizing agent packed layer) with a universally known zinc oxide type adsorption desulfurizing agent, or the like, so that sulfur compounds that can be adsorbed by zinc oxide, etc., are removed beforehand.

According to this method, the hydrogen sulfide, etc., contained in town gas that is manufactured using coal gas, etc., as a starting material, can be removed by means of zinc oxide, etc. Accordingly, the load on the copper-zinc-X type desulfurizing agent (or copper-zinc-aluminum-X type desulfurizing agent) can be reduced so that the useful life of the desulfurizing agent can be extended. Furthermore, even in cases where mercaptan type sulfur compounds are contained in the raw-material gas, such compounds can be adsorbed on zinc oxide. Accordingly, the load on the copper-zinc-X type desulfurizing agent (or copper-zinc-aluminum-X type desulfurizing agent) can be reduced, so that the useful life of the desulfurizing agent can be extended.

In cases where the sulfur content in the raw material is large, it is desirable to pack the area on the upstream side of the copper-zinc-X type desulfurizing agent (or copper-zinc-aluminum-X type desulfurizing agent) with a universally known Co—Mo catalyst or Ni—Mo catalyst and a zinc oxide adsorbing agent, and to lower the sulfur content to the level of a few ppm beforehand by means of a conventional hydrodesulfurization method.

The adsorbing agents of the present invention exhibit a high adsorbing performance that is difficult or impossible to achieve using conventional adsorbing agents. Accordingly, the desulfurizing agents of the present invention show a conspicuous effect especially in cases where these agents are used as secondary desulfurizing agents that perform a higher degree of desulfurization after the hydrocarbon raw material has been desulfurized as far as possible by using ordinary methods.

Examples of hydrocarbon raw materials that can be purified by the method of the present invention include various types of town gas (in the present description, this term refers to gases consisting of at least one $C_1$ to $C_5$ hydrocarbon, as well as mixed gases consisting principally of such hydrocarbons, which are supplied to municipalities), natural gas, ethane, propane, butane, LPG, light naphtha, full-range naphtha and COG, etc.

Effect of the Invention

The copper-zinc-X type desulfurizing agent and copper-zinc-aluminum-X type desulfurizing agent of the present invention are extremely superior in terms of hydrocarbon desulfurization performance. Accordingly, these agents show effects permitting highly desulfurized hydrocarbons to be obtained easily and in a stable manner over a long period of time by using small quantities of these desulfurizing agents. Consequently, even in cases where catalysts that are susceptible to sulfur poisoning are used in the steam reforming of hydrocarbon raw material, etc., the deleterious effects of sulfur can be eliminated to a great extent; e.g., sulfur poisoning can be virtually completely prevented, etc.

BEST MODE FOR CARRYING OUT THE INVENTION

Below, the present invention will be described in greater detail in terms of examples and comparative examples. It goes without saying that the present invention is not limited by these examples.

Example 1

A mixed aqueous solution containing copper nitrate and zinc nitrate at a ratio (molar ratio) of 1:1 (respective concentrations: 0.5 mol/liter) was added dropwise under agitation to an aqueous solution of sodium carbonate (concentration: 0.6 mol/liter) maintained at a temperature of about 60° C., thus producing a precipitate. This precipitate was thoroughly washed with water, filtered and dried. The dried precipitate was calcined at a temperature of about 280° C., and was added to water so that a slurry was prepared. This slurry was filtered and dried; then a binder (graphite) was added, and the dried material was extruded into a shaped form having a diameter of ⅛ inch.

The shaped form thus obtained was impregnated with an aqueous solution of nickel nitrate (Ni concentration: 0.2 mol/liter), and was then dried. This formed body was then calcined at a temperature of approximately 300° C., thus producing a desulfurizing agent precursor. The nickel content of this desulfurizing agent precursor was 5 wt %. Nitrogen gas containing 2 vol % hydrogen was passed through a desulfurization tube filled with 100 cc of this desulfurizing agent precursor (length of desulfurizing layer: 20 cm), and a reduction treatment was performed at a temperature of 200° C., thus producing a desulfurizing agent.

Town gas (13A gas) consisting of the composition shown in Table 1 was desulfurized using this desulfurizing agent at a GHSV of 1200 $h^{-1}$, a hydrogen/town gas ratio of 0.01 (molar ratio), a pressure of 0.02 kg/cm2.G, and a temperature of 250° C.

TABLE 1

| Methane | 86.9 vol % |
|---|---|
| Ethane | 8.1 vol % |
| Propane | 3.7 vol % |
| Butane | 1.3 vol % |
| Odorizing agents | |
| Dimethyl sulfide | 3 mg · S/Nm$^3$ |
| t-Butylmercaptan | 2 mg · S/Nm$^3$ |

When the sulfur content in the town gas after desulfurization was measured continuously, it was found that this content was always 0.1 ppb or less in 8000 hours of operation.

The sulfur content in the town gas after desulfurization was measured by quantitative analysis based on gas chromatography using a flame photometric detector (FPD).

This method was performed using the following procedure. First, a fixed amount of the desulfurized town gas was passed at a fixed velocity through a U-shaped glass tube immersed in a dry ice-ethanol coolant. In this case, the hydrocarbons, which had dew points that were lower than the temperature of the dry ice-ethanol (196 K) passed through the U-shaped tube, while the sulfur compounds were trapped and concentrated inside the U-shape tube. After a sufficient quantity of sulfur compounds had been concentrated inside the U-shaped tube, the outlet of the U-shape tube was connected to the gas introduction part of the FPD-gas chromatograph, and the U-shaped tube was rapidly heated, with the coolant being removed while a carrier gas was caused to flow through. The sulfur compounds trapped in the U-shaped tube were carried into the FPD-gas chromatograph by the carrier gas, and a quantitative analysis was performed in this FPD-gas chromatograph. The lower limit of detection of this method also depends on the concentration method that is used; however, this limit is about 0.1 ppb for a 100-fold concentration. This quantitative analysis method for the sulfur concentration will be referred to below as the "cold trap method".

Example 2

A mixed aqueous solution containing copper nitrate, zinc nitrate and aluminum hydroxide at a ratio (molar ratio) of 1:1:0.3 (respective concentrations: 0.5 mol/liter) was added dropwise under agitation to an aqueous solution of sodium carbonate (concentration: 0.6 mol/liter) maintained at a temperature of about 60° C., thus producing a precipitate. This precipitate was thoroughly washed with water, filtered and dried.

The dried precipitate was calcined at a temperature of approximately 280° C., and was added to water to prepare a slurry. This slurry was filtered and dried; then, a binder (graphite) was added. The resultant material was extruded into a formed body having a diameter of ⅛ inch.

The formed body thus obtained was impregnated with an aqueous solution of nickel nitrate (Ni concentration: 0.2 mol/liter), and was then dried. The dried formed body was then calcined at a temperature of approximately 300° C., thus producing a desulfurizing agent precursor. The nickel content of this desulfurizing agent precursor was 5 wt %. Nitrogen gas containing 2 vol % hydrogen was passed through a desulfurization tube filled with 100 cc of this desulfurizing agent precursor (length of desulfurizing layer: 20 cm), and a reduction treatment was carried out at a temperature of 200° C., thus producing a desulfurizing agent.

Town gas (13A gas) having the composition shown in Table 1 was desulfurized with using this desulfurizing agent at a GHSV of 1200 $h^{-1}$, a hydrogen/town gas ratio of 0.01 (molar ratio), a pressure of 0.02 kg/cm$^2$·G, and a temperature of 250° C. When the sulfur content in the gas after desulfurization was measured continuously by the cold trap method, it was found that this content was always 0.1 ppb or less in 8000 hours of operation.

Example 3

A mixed aqueous solution containing copper nitrate and zinc nitrate at a ratio of 1:1 (molar ratio) was added dropwise under agitation to an aqueous solution of sodium carbonate (concentration: 0.6 mol/liter) maintained at a temperature of approximately 60° C., thus producing a precipitate. This precipitate was thoroughly washed with water, filtered and dried. The dried precipitate was calcined at a temperature of about 280° C., and was added to water to prepare a slurry. This slurry was filtered and dried; then, a binder (graphite) was added. The dried material thus obtained was extruded into a shaped form having a diameter of ⅛ inch.

The shaped form thus obtained was impregnated with an aqueous solution of iron nitrate (iron concentration: 0.2 mol/liter), and was then dried. The shaped form thus dried was calcined at a temperature of about 300° C., a desulfurizing agent precursor was obtained thereby. The iron content in this desulfurizing agent precursor was 5 wt %. Nitrogen gas containing 2 vol % hydrogen was passed through a desulfurization tube loaded with 100 cc of this desulfurizing agent precursor (length of desulfurizing layer: 20 cm), and a reduction treatment was performed at a temperature of 200° C., so that a desulfurizing agent was produced.

Town gas (13A gas) having the composition shown in Table 1 was desulfurized using this desulfurizing agent at a GHSV of 1200 $h^{-1}$, a hydrogen/town gas ratio of 0.01 (molar ratio), a pressure of 0.02 kg/cm$^2$≅G, and a temperature of 250° C.

When the sulfur content in the gas after desulfurization was measured continuously by the cold trap method, it was found that this content was always 0.1 ppb or less in 6000 hours of operation.

Comparative Example 1

A mixed aqueous solution containing copper nitrate and zinc nitrate at a ratio of 1:1 (molar ratio) was added dropwise under agitation to an aqueous solution of sodium carbonate (concentration: 0.6 mol/liter) maintained at a temperature of about 60° C. The precipitate thus produced was washed, filtered and dried, and was then extruded into a formed body with a diameter of ⅛ inch. This formed body was calcined at a temperature of about 300° C.

Nitrogen gas containing 2 vol % hydrogen was passed through a desulfurization tube packed with 100 cc of this calcined body (length of desulfurizing layer: 20 cm), and a reduction treatment was performed at a temperature of 200° C., thus producing a desulfurizing agent.

Town gas (13A gas) consisting of the composition shown in Table 1 was desulfurized using this desulfurizing agent at a GHSV of 1200 $h^{-1}$, a hydrogen/town gas ratio of 0.01 (molar ratio), a pressure of 0.02 $kg/cm^2 \cdot G$, and a temperature of 250° C.

When the sulfur content in the gas following desulfurization was measured continuously, the content was 21 ppb after 1260 hours had elapsed, and the sulfur content subsequently increased even further.

Comparative Example 2

A mixed aqueous solution containing copper nitrate and zinc nitrate at a ratio of 1:1 (molar ratio) was added dropwise under agitation to an aqueous solution of sodium carbonate (concentration: 0.6 mol/liter) maintained at a temperature of approximately 60° C. The precipitate thus produced was washed, filtered and dried, and powdered nickel oxide was then mixed with the precipitate. This mixture was then extruded into a shaped form having a diameter of ⅛ inch. This shaped form was calcined at a temperature of approximately 300° C., thus producing a desulfurizing agent precursor. The nickel content in this desulfurizing agent precursor was 5 wt %.

Nitrogen gas containing 2 vol % hydrogen was passed through a desulfurization tube filled with 100 cc of this desulfurizing agent precursor (length of desulfurizing layer: 30 cm), and a reduction treatment was performed at a temperature of 200° C., thus producing a desulfurizing agent.

Town gas (13A gas) having the composition shown in Table 1 was desulfurized with using this desulfurizing agent at a GHSV of 1200 $h^{-1}$, a hydrogen/town gas ratio of 0.01 (molar ratio), a pressure of 0.02 $kg/cm^2 \cong G$, and a temperature of 250° C.

When the sulfur content in the gas after desulfurization was measured continuously, the content was 21 ppb after 2200 hours had elapsed, and the sulfur content subsequently increased even further.

Example 4

A mixed aqueous solution containing copper nitrate, zinc nitrate and aluminum nitrate at a ratio of 1:1:0.3 (molar ratio) (respective concentrations: 0.5 mol/liter, 0.5 mol/liter and 0.15 mol/liter) was added dropwise under agitation to an aqueous solution of sodium carbonate (concentration: 0.6 mol/liter) maintained at a temperature of about 60EC, thus producing a precipitate. This precipitate was thoroughly washed with water, filtered and dried.

The dried precipitate was calcined at a temperature of approximately 350° C., and was then added to water so that a slurry was prepared. This slurry was filtered and dried, a binder was then added. The dried material was formed into a tablet having a diameter of ¼ inch and a length of ⅛ inch. This tablet was impregnated with an aqueous solution of nickel nitrate (Ni concentration: 0.3 mol/liter), and was then dried and calcined at a temperature of about 300° C., thus producing a desulfurizing agent precursor. The nickel content in this desulfurizing agent precursor was 7 wt %.

Nitrogen gas containing 2 vol % hydrogen was passed through a desulfurization tube packed with 1000 cc of the desulfurizing agent precursor thus obtained (length of desulfurizing layer: 200 cm), and a reduction treatment was performed at a temperature of about 200° C., thus producing a desulfurizing agent.

With using this desulfurizing agent, hexane containing 0.1 mg-S/liter thiophene was desulfurized at an LHSV of 1.7, a hydrogen/hexane ratio of 0.3 (molar ratio), a pressure of 9.5 $kg/cm^2 \cdot G$, and a temperature of about 370° C.

When the sulfur content in the desulfurized hexane thus obtained was measured continuously by a total sulfur analyzer (manufactured by Houston Atlas Co.), it was found that this content was always less than the detection limit (0.005 mg-S/liter) in 4000 hours of operation.

Example 5

By using a desulfurizing agent prepared in the same manner as in Example 4, hexane containing 0.1 mg-S/liter benzothiophene was desulfurized at an LHSV of 1.7, a hydrogen/hexane ratio of 0.3 (molar ratio), a pressure of 9.5 $kg/cm^2 \cdot G$, and a temperature of about 370° C.

When the sulfur content in the desulfurized hexane thus obtained was measured continuously by using a total sulfur analyzer (manufactured by Houston Atlas Co.), this content was always less than the detection limit (0.005 mg-S/liter) in 4000 hours of operation.

Example 6

A mixed aqueous solution containing copper nitrate, zinc nitrate and aluminum hydroxide at a ratio of 1:1:0.3 (molar ratio) was added dropwise under agitation to an aqueous solution of sodium carbonate (concentration: 0.6 mol/liter) maintained at a temperature of approximately 60° C., thus producing a precipitate. This precipitate was thoroughly washed with water, filtered and dried.

The dried precipitate was calcined at a temperature of approximately 280° C., and was then added to water to prepare a slurry. This slurry was filtered and dried; then, a binder (graphite) was added. The dried material was granulated into granules having a size of about 1 to 2 mm. The granules were impregnated with an aqueous solution of nickel nitrate (Ni concentration: 0.2 mol/liter), and was then dried and calcined at a temperature of approximately 300° C., thus producing a desulfurizing agent precursor. The nickel content in this desulfurizing agent precursor was 5 wt %. A micro-reactor (internal diameter: 0.6 inches) was filled with 1 cc of this desulfurizing agent precursor. Nitrogen gas containing 2 vol % hydrogen was passed through this micro-reactor, and a reduction treatment was performed at a temperature of 200° C., thus producing a desulfurizing agent.

A mixed gas having the composition shown in Table 2 was passed through a reaction tube packed with this desulfurizing agent at a GHSV of 2500 h$^{-1}$, a pressure of 1 kg/cm$^2$·G, and a temperature of 350° C., and the composition of the gas at the outlet was analyzed by means of a gas chromatograph. As a result, it was found that the CO concentration in the outlet gas was 1.8 vol %; furthermore, almost no rise in temperature due to a methane forming reaction was seen.

TABLE 2

| | |
|---|---|
| Nitrogen | 90.0 vol % |
| CO | 2.0 vol % |
| Hydrogen | 8.0 vol % |

Comparative Example 3

A mixed aqueous solution containing copper nitrate, zinc nitrate and aluminum hydroxide at a ratio of 1:1:0.3 (molar ratio) was added dropwise under agitation to an aqueous solution of sodium carbonate (concentration: 0.6 mol/liter) maintained at a temperature of about 60EC, thus producing a precipitate. This resultant precipitate was thoroughly washed with water, filtered and dried. Next, the dried precipitate was calcined at a temperature of about 280° C., and added to water so that a slurry was prepared. This slurry was filtered and dried. Powdered nickel oxide was mixed with the dried mixed oxide thus obtained; then, a binder (graphite) was added. The mixture was granulated to form granules having a size of approximately 1 to 2 mm. The granules were dried, and was then calcined at a temperature of approximately 300EC, thus producing a desulfurizing agent precursor. The nickel content in this desulfurizing agent precursor was 5 wt %.

A micro-reactor (internal diameter: 0.6 inch) was packed with 1 cc of this desulfurizing agent precursor. Nitrogen gas containing 2 vol % hydrogen was passed through this micro-reactor, and a reduction treatment was performed at a temperature of 200° C., thus producing a desulfurizing agent.

When a mixed gas consisting of the composition shown in Table 2 was passed through a reaction tube packed with this desulfurizing agent under the same conditions as in Example 6. The CO concentration in the outlet gas was approximately 0 vol %, and a conspicuous temperature rise caused by a methane forming reaction was observed.

Comparative Example 4

A micro-reactor (internal diameter: 0.6 inch) was packed with 1 cc of a commercial marketed nickel catalyst supported on alumina (nickel content: 20 wt %). Nitrogen gas containing 2 vol % hydrogen was passed through this micro-reactor, and a reduction treatment was performed at a temperature of approximately 200° C., thus producing a desulfurizing agent.

When a mixed gas having the composition shown in Table 2 was passed through a reaction tube packed with this desulfurizing agent under the same conditions as in Example 6, the CO concentration in the outlet gas was approximately 0 vol %, and a conspicuous temperature rise caused by a methane forming reaction was observed.

Comparative Example 5

A mixed aqueous solution containing copper nitrate, zinc nitrate and nickel nitrate at a ratio of 1:1:0.3 (molar ratio) and an aqueous solution of sodium carbonate (concentration: 0.6 mol/liter) were simultaneously added dropwise at a constant rate under agitation to purified water maintained at a temperature of about 60° C. The precipitate thus produced by co-precipitation was washed, filtered and dried; then, this dried precipitate was calcined at a temperature of approximately 280° C. The calcined product was added to water so that a slurry was prepared, and this slurry was then filtered and dried. A binder (graphite) was added to the dried product thus obtained, and this dried product was formed into granules having a size of approximately 1 to 2 mm. The nickel content of this desulfurizing agent precursor was 5 wt %.

A micro-reactor (internal diameter: 0.6 inch) was filled with 1 cc of this desulfurizing agent precursor. Nitrogen gas containing 2 vol % hydrogen was passed through this micro-reactor, and a reduction treatment was performed at a temperature of about 200° C., thus producing a desulfurizing agent.

When a mixed gas consisting of the composition shown in Table 2 was passed through a reaction tube filled with this desulfurizing agent under the same conditions as in Example 6, the CO concentration in the outlet gas was 1.5 vol %, and a temperature rise caused by a methane forming reaction was observed.

Comparative Example 6

A mixed aqueous solution containing copper nitrate, zinc nitrate and aluminum nitrate at a ratio of 1:1:0.3 (molar ratio) was added dropwise under agitation to an aqueous solution of sodium carbonate (concentration: 0.6 mol/liter) maintained at a temperature of approximately 60° C. The precipitate thus produced was washed, filtered and dried. The dried precipitate was then formed into a tablet having a diameter of ¼ inch and a length of ⅛ inch, and the tablet was calcined at a temperature of about 400° C. Nitrogen gas containing 2 vol % hydrogen was passed through a desulfurization tube filled with 1000 cc of the calcined body (length of desulfurizing layer: 200 cm), and a reduction treatment was carried out at a temperature of about 200EC. Thus, a desulfurizing agent was obtained.

Hexane containing thiophene at the rate of 0.1 mg-S/liter was desulfurized with using the desulfurizing agent at an LHSV of 1.7, a hydrogen/hexane ratio of 0.3 (molar ratio), a pressure of 9.5 kg/cm$^2$≅G, and a temperature of 370° C. When the sulfur content in the hexane after desulfurization was measured continuously, the content was 0.01 mg-S/liter after 455 hours had elapsed, and the sulfur content subsequently increased.

Example 7

A raw material for a fuel cell power generating system was subjected to a desulfurization test. The desulfurization apparatus used as a desulfurization apparatus loaded with 38 liters of a copper-zinc-aluminum-nickel desulfurizing agent obtained by the same method of manufacture as in Example 1 (length of desulfurizing layer: about 76 cm).

As a raw material, town gas 13A consisting of the components shown in the abovementioned Table 1 (12 Nm$^3$/h, GHSV=320 h$^{-1}$) was preheated to a temperature of about 200° C. The gas was introduced into the desulfurization apparatus together with a recycled gas containing 1 Nm$^3$/h hydrogen, and was desulfurized. The desulfurized gas was supplied to a steam reforming reaction at an S/C ratio of 3.0, reaction temperatures of 450° C. (inlet) and 665° C. (outlet), and a reaction pressure of 0.1 kg/cm$^2$.

The fuel gas that had been subjected to the steam reforming treatment was converted at a converter outlet temperature of 190° C. and a reaction pressure of 0.05 kg/cm$^2$ in a heat exchange reactor type carbon monoxide converter packed with a commercially marketed low-temperature carbon monoxide conversion catalyst. Afterward, the gas was conducted to the fuel pole of the fuel cell main body, and was reacted with oxygen in the air pole introduced into the oxidation pole, so that electrical energy was obtained.

When the sulfur content in the gas at the outlet of the desulfurization apparatus was measured continuously, this sulfur content was 0.1 ppb or less even after 20,000 hours had elapsed; the steam reforming catalyst maintained a high activity comparable to the activity seen immediately after the initiation of the reaction, and the fuel cell operated normally.

The inventon claimed is:

1. A hydrocarbon desulfurization method, said method comprising:
    desulfurizing a hydrocarbon raw material comprising methane, ethane, propane and butane, in the presence of hydrogen using a sulfur-adsorption type desulfurizing agent manufactured by a method comprising:
        mixing a mixture containing a copper compound, a zinc compound and an aluminum compound with an aqueous solution of an alkali substance to prepare a precipitate,
        calcining the resultant precipitate,
        forming the calcined precipitate into a shaped form of a copper oxide-zinc oxide-aluminum oxide mixture,
        impregnating the shaped form with iron and/or nickel,
        calcining the impregnated form to produce a calcined oxide, and
        reducing the calcined oxide with hydrogen to form the sulfur-adsorption type desulfurizing agent,
    wherein the desulfurization is performed at a space velocity (GHSV) of 200 to 10,000 $h^{-1}$.

2. The hydrocarbon desulfurization method according to claim 1, wherein the hydrogen present in an amount such that the hydrogen/hydrocarbon raw material molar ratio is 0.0005 to 0.4.

3. The hydrocarbon desulfurization method according to claim 1, wherein desulfurization is performed at a pressure of 0.05 to 50 atm, and a temperature of 100 to 400° C.

4. The hydrocarbon desulfurization method according to claim 1, wherein the raw material hydrocarbon is town gas, and an amount of hydrogen is present so that the hydrogen/town gas molar ratio is 0.0005 to 0.4.

5. The desulfurization method according to claim 4, wherein desulfurization is performed at a pressure of 0.05 to 50 atm, and a temperature of 100 to 400° C.

6. The desulfurization method according to claim 5, wherein desulfurization is performed so that the sulfur content in the town gas is not more than 5 ppb (vol ppb).

7. The method of claim 1, wherein the sulfur-adsorption type desulfurizing agent is chemically changed due to the adsorption of sulfur.

8. A method for producing a sulfur-adsorption type desulfurizing agent, said method comprising:
    mixing a mixture containing a copper compound, a zinc compound and an aluminum compound with an aqueous solution of an alkali substance to prepare a precipitate,
    calcining the resultant precipitate,
    forming the calcined precipitate into a shaped form of a copper oxide-zinc oxide-aluminum oxide mixture,
    impregnating the shaped form with iron and/or nickel,
    calcining the impregnated form to produce a calcined oxide, and
    reducing the calcined oxide with hydrogen, to form the sulfur-adsorption type desulfurizing agent,
    wherein the sulfur-adsorption type desulfurizing agent adsorbs sulfur present in hydrocarbons, when exposed to the hydrocarbons in the presence of hydrogen.

9. The method of claim 8, further comprising washing the precipitate with water prior to calcining the resultant precipitate.

10. The method of claim 8, further wherein the impregnating the shaped form with iron and/or nickel, comprises impregnating with iron and/or nickel in the range of 1 to 10 wt %.

11. The method of claim 8, wherein the sulfur-adsorption type desulfurizing agent is chemically changed when the agent adsorbs sulfur.

12. A hydrocarbon desulfurization method, said method comprising:
    mixing a mixture containing a copper compound, a zinc compound and an aluminum compound with an aqueous solution of an alkali substance to prepare a precipitate,
    calcining the resultant precipitate,
    forming the calcined precipitate into a shaped form of a copper oxide-zinc oxide-aluminum oxide mixture,
    impregnating the shaped form with iron and/or nickel,
    calcining the impregnated form to produce a calcined oxide,
    reducing the calcined oxide with hydrogen, to form a sulfur-adsorption type desulfurizing agent, and
    desulfurizing a hydrocarbon raw material comprising methane, ethane, propane and butane, in the presence of hydrogen using the desulfurizing agent,
    wherein the desulfurization is performed at a space velocity (GHSV) of 200 to 10,000 $h^{-1}$.

13. The method of claim 12, wherein the hydrogen is present in an amount such that the hydrogen/hydrocarbon raw material molar ratio is 0.0005 to 0.4.

14. The method to claim 12, wherein desulfurization is performed at a pressure of 0.05 to 50 atm, and a temperature of 100 to 400° C.

15. The method according to claim 12, wherein the raw material hydrocarbon is town gas, and an amount of hydrogen is present so that the hydrogen/town gas molar ratio is 0.0005 to 0.4.

16. The method according to claim 12, wherein desulfurization is performed at a pressure of 0.05 to 50 atm, and a temperature of 100 to 400° C.

17. The method according to claim 16, wherein desulfurization is performed so that the sulfur content in the town gas is not more than 5 ppb (vol ppb).

* * * * *